(12) United States Patent
Reichel et al.

(10) Patent No.: US 9,074,981 B2
(45) Date of Patent: Jul. 7, 2015

(54) SENSOR ARRANGEMENT FOR MEASURING PROPERTIES OF FLUIDS

(75) Inventors: Erwin Reichel, Leuven (BE); Bernhard Jakoby, Linz (AT); Christian Riesch, Feldkirch (AT)

(73) Assignee: Johannes Kepler Universitaet, Linz (AT)

( * ) Notice: Subject to any disclaimer, the term of this patent is extended or adjusted under 35 U.S.C. 154(b) by 304 days.

(21) Appl. No.: 13/392,660

(22) PCT Filed: Aug. 20, 2010

(86) PCT No.: PCT/EP2010/062192
§ 371 (c)(1),
(2), (4) Date: Feb. 27, 2012

(87) PCT Pub. No.: WO2011/023642
PCT Pub. Date: Mar. 3, 2011

(65) Prior Publication Data
US 2012/0152001 A1 Jun. 21, 2012

(30) Foreign Application Priority Data
Aug. 27, 2009 (AT) ................ A 1345/2009

(51) Int. Cl.
*G01N 11/16* (2006.01)
(52) U.S. Cl.
CPC ..................... *G01N 11/16* (2013.01)
(58) Field of Classification Search
CPC ............... G01N 11/16; G01N 11/162
USPC .............................. 73/54.41, 64.53
See application file for complete search history.

(56) References Cited

U.S. PATENT DOCUMENTS

| | | |
|---|---|---|
| 3,496,762 A | 2/1970 | Gaeta |
| 3,943,753 A | 3/1976 | Simon |
| 4,862,384 A | 8/1989 | Bujard |
| 5,365,778 A | 11/1994 | Sheen et al. |
| 5,698,773 A | 12/1997 | Blom et al. |

(Continued)

FOREIGN PATENT DOCUMENTS

EP 0 681 176 A1 11/1995

OTHER PUBLICATIONS

Authors: Frieder Lucklum and Bernhard Jakoby, Title: Multi-Mode Excitation of Electromagnetic-Acoustic Resonant Sensor Arrays, Date: 2008, Publisher: IEEE, pp. 53-57.*

(Continued)

*Primary Examiner* — Harshad R Patel
(74) *Attorney, Agent, or Firm* — Laurence A. Greenberg; Werner H. Stemer; Ralph E. Locher (57) ABSTRACT

A sensor array for viscosity measurement includes the following: a carrier substrate formed with an opening; a metal plate-shaped oscillating element disposed on a surface of the carrier substrate and parallel to the surface over the opening; at least two metal contact electrodes disposed on the carrier substrate; at least two metal spring elements, wherein each of the contact electrodes is connected to the oscillating element by way of a spring element such that the element is mounted on the carrier substrate by way of the spring elements; and a magnet, which is disposed in the vicinity of the carrier substrate such that the magnetic field lines penetrate the plate-shaped oscillating element.

29 Claims, 5 Drawing Sheets

(56) References Cited

U.S. PATENT DOCUMENTS 6,393,913 B1 * 5/2002 Dyck et al. .............. 73/504.12
2005/0262943 A1 * 12/2005 Claydon et al. .............. 73/579

OTHER PUBLICATIONS

Reichel, et al., "Optimized design of quartz disc viscosity sensors for the application in harsh chemical environments", Proceedings of the International Congress on Ultrasonics, Apr. 9-13, 2007, pp. 1-4, Vienna, Austria.

Riesch, et al., "A suspended plate viscosity sensor featuring in-plane vibration and piezoresistive readout", Journal of Micromechanics and Microengineering, Jun. 2009, pp. 1-10, IOP Publishing, UK.

Lucklum, et al., "Novel magnetic-acoustic resonator sensor for remote liquid phase measurement and mass detection", Sensors and Actuators, Oct. 2007, pp. 44-51, Elsevier, Institute for Microelectronics, Johannes Kepler University, Linz, Austria.

Ronaldson, et al., "Transversely Oscillating MEMS Viscometer: The Spider", International Journal of Thermophysics, Nov. 2006, pp. 1677-1695, vol. 27, No. 6, Springer Science + Business Media, Inc.

Agoston, et al., "Evaluation of a vibrating micromachined cantilever sensor for measuring the viscosity of complex organic liquids", Sensors and Actuators, Mar. 2005, pp. 82-86, Science Direct.

Seo, et al., "High Q-Factor In-Plane-Mode Resonant Microsensor Platvorm for Gaseous/Liquid Environment", Journal of Microelectromechanical Systems, Apr. 2008, pp. 483-493, vol. 17, No. 2, IEEE.

\* cited by examiner

SENSOR ARRANGEMENT FOR MEASURING PROPERTIES OF FLUIDS

The invention relates to a micromechanical sensor arrangement for use in process measuring technology, in particular a sensor arrangement with a micromechanical, metal resonator excited with the aid of Lorentz forces for measuring the viscosity and/or density of liquids.

BACKGROUND

Viscoelastic properties of liquids, in particular including those with complex flow behavior (such as for example non-Newtonian fluids), are usually measured in the laboratory, for example with the aid of oscillating viscometers. The oscillating properties of an oscillating body under the influence of the viscous liquid are in this case measured up to a frequency of several hundred hertz. To determine the viscosity, it may be necessary to know the density of the liquid or measure it at the same time.

In process measuring technology, MEMS components or oscillating quartz crystals, which typically operate at much higher frequencies, such as for example at several megahertz in the case of TSM oscillating quartz crystals (TSM stands for: "thickness shear mode"), are used as viscosity sensors for the online monitoring of processes. For this reason, viscosity sensors that are available at present for process measuring technology are mainly used in the monitoring of simple (Newtonian) liquids, the viscous behavior of which can be described by a single viscosity parameter (for example the dynamic viscosity r). However, the measurement results achieved with such sensors at high frequencies for the viscosity of non-Newtonian fluids often cannot be compared with reference values determined in the laboratory.

In the latest developments it is being attempted to use spring-mounted oscillating plates produced by semiconductor technology at lower oscillating frequencies (to about 16 kHz) for viscosity measurement, the oscillating amplitude being measured with the aid of piezoresistive silicon layers. However, such sensors are complex to produce and, among other things, present difficulties with conducting liquids.

The object on which the invention is based is to provide a sensor arrangement that can be used in process measuring technology for measuring physical properties of liquids, in particular viscosity, which is easy to produce and which can be operated at such low frequencies that the measured values achieved can be compared with conventionally determined laboratory values.

SUMMARY OF THE INVENTION

This object is achieved by a sensor arrangement for viscosity or density measurement and by a measuring method.

According to one example of the invention, a sensor arrangement for measuring properties (for example viscosity, density) of liquids comprises the following: a carrier substrate with an opening; a metal, plate-shaped oscillating element, which is disposed on a surface of the carrier substrate and parallel thereto over the hole; at least two metal contact electrodes, which are disposed on the carrier substrate; at least two metal spring elements, the contact electrodes being respectively connected to the oscillating element by way of a spring element, so that said oscillating element is mounted on the carrier substrate by way of the spring elements; and a magnet, which is disposed in the vicinity of the carrier substrate in such a way that the magnetic field lines pass through the plate-shaped oscillating element.

A sensor built up according to the invention is suitable for rapid online measurements of, for example, viscosity and/or density in process measuring technology. If a suitable metal is used, the sensor can be of a high-temperature-resistant and/or acid-resistant form. The amount of liquid required for a measurement is very small. The sensor can be produced at low cost and, if required, also be installed in a handheld device. On account of the metal oscillating element, the sensor arrangement may also be used for measurements in conductive liquids.

A further example of the invention concerns a method for measuring properties of liquids, such as for example viscosity and/or density, with a sensor arrangement which has at least the aforementioned features. The method comprises the following steps: feeding the excitation current with an adjustable frequency into the oscillating element by way of the spring elements, so that a resonance of the oscillating element is excited; measuring the voltage induced in the oscillating element on account of the in-plane oscillation for different frequencies of a prescribed frequency range of the excitation current; determining a frequency response for the induced voltage over the prescribed frequency range and detecting a resonance in the frequency response or determining a frequency response for the ratio of induced voltage and excitation current over the prescribed frequency range and detecting a resonance in the frequency response; calculating a characteristic value characterizing the detected resonance; calculating a property that describes the physical behavior of the liquid surrounding the oscillating element and is dependent on the characteristic value.

A characteristic value characterizing the resonance may be, for example, the resonant frequency or a damping factor of the resonance (or the quality factor). A property describing the physical behavior of the liquid may be, for example, the dynamic viscosity or density thereof. The oscillation measurement by way of the voltage induced in the oscillating element allows a simple and low-cost structure of the sensor.

BRIEF DESCRIPTION OF THE FIGURES

The invention is explained in more detail below on the basis of exemplary embodiments that are represented in the figures, in which:

FIG. 2 shows (a) measurement results for the resonance of the sensor element from FIG. 1 and (b) the relationship between damping of the resonance and viscosity;

In the figures, the same reference numerals designate the same components or signals with the same meaning.

DETAILED DESCRIPTION

The exemplary embodiments of the present invention that are described below concern a sensor arrangement for viscosity measurement. With minor modifications, which will be further discussed later at the end, however, it is also possible in addition to measure the mass per unit area (i.e. the density) of the liquid.

The sensor arrangement according to the invention makes it possible to measure the viscosity at oscillating frequencies of several kilohertz (for example 0 to 20 kHz), and consequently on the one hand makes it possible to determine viscosity values that can be compared with measured values of high-quality laboratory measuring instruments and on the other hand closes the gap in terms of frequency with known viscosity sensors operating at high frequency.

The basic structure of a sensor arrangement 100 given by way of example for measuring the viscosity and/or the density of a fluid is explained below on the basis of the schematic perspective representation in FIG. 1. The sensor arrangement 100 from FIG. 1 comprises a sensor element 1, which interacts with the viscous fluid, and the electronics necessary for operating the sensor element 1 (for example function generator 30, lock-in amplifier).

The sensor element 1 itself comprises, inter alia, a plate-shaped oscillating element 12 (i.e. a metal membrane), which is mounted with the aid of at least two—in the present case four—spring elements 13. The oscillating element 12 and the four spring elements 13 consist completely of metal or a metal alloy (for example nickel-brass), which is accompanied by a comparatively great mass (measured in terms of the spatial size of the sensor element) and a correspondingly good electrical conductivity. Optionally, a gold coating may improve the surface properties (for example the corrosion resistance) of the oscillating element 12. A suitable choice of the metal (for example tantalum) makes a temperature-resistant sensor possible, for measurements at high temperatures. In addition, if required, for example for passivating purposes, the sensor element 1 may also be provided with nonconducting layers. A metal oscillating element should be understood as meaning that the oscillating body itself (i.e. the oscillating structural element as a whole) consists substantially (i.e. apart from a possibly present passivating layer) of a metal. In this way, the oscillating element differs, for example, from known sensor arrangements in which the oscillating body consists, for example, of a semiconductor (silicon) or an insulator on which conductor tracks have to be separately applied.

The sensor arrangement 100 further comprises for at least two (in the case presented four) of the spring elements 13 corresponding contact electrodes 14, which lie in one plane with the oscillating element 12 and the spring elements 13 and may be made of the same material. The contact electrodes 14 are disposed on a carrier substrate 15 (not represented in FIG. 1; also see FIG. 4) and serve for the electrical contacting of the sensor element 1 by way of the spring elements 13 to the sensor electronics (for example function generator 30, lock-in amplifier). The carrier substrate may be a simple circuit board (FR4 material of glass fiber-reinforced epoxy resin), as is also used for printed circuits, but—depending on the application—other materials may also be used (for example ceramic for applications with higher temperatures). The fact that the oscillating element is produced from metal also allows measuring in conductive liquids, as long as the conductivity of the liquid is negligible in comparison with the conductivity of the metal. This is almost always the case in practical applications. If necessary, the oscillating element may also be coated with a passivating insulating layer.

The oscillating element 12, the spring elements 13 and the contact electrodes 14 may be produced from a thin metal layer (for example 100 μm in thickness), for example with the aid of wet etching methods. Details of the production of the sensor arrangement 100 are described more precisely further below on the basis of FIG. 4.

A magnet is disposed parallel to the plane of the oscillating element 12 in such a way that the magnetic field generated by it passes through the oscillating element 12. The magnetic field lines are in this case approximately at right angles to the plane of the plate of the plate-shaped oscillating element 12. The use of a permanent magnet 11 makes a simple and compact structure of the sensor element 1 possible.

For the electronic activation, two of the contact electrodes (in FIG. 1 the two on the left) are connected, for example, to a function generator 30, which generates an alternating current $i_{EX}$ through the plate-shaped oscillating element 12 as the excitation current. The resultant current density vector J lies in the plane of the plate of the oscillating element 12 and points approximately from the first to the second spring element 13 through which the current $i_{EX}$ is flowing. If—as mentioned above—the magnetic field B of the magnet 11 passes approximately at a right angle through the plane of the oscillating element 12, the Lorentz force $F_L$ acting on the oscillating element 12 likewise lies in the plane of the plate of the oscillating element 12. A corresponding oscillation is in this way excited in the plane of the plate of the oscillating element 12 (in-plane oscillation).

In simple terms, the spring-mounted oscillating element 12 immersed in viscous liquid forms a spring-mass-damper system, the resonant frequency of which depends on the mass of the oscillating element 12, the effective spring constant of the resilient suspension of the oscillating element 12 with the aid of the spring elements 13 and the damping. The damping of the system—and with it the quality factor (Q factor) of the resonance—is thereby substantially determined by the viscosity of the viscous liquid surrounding the oscillating element 12.

To be able to evaluate the damping of the system, and draw conclusions from it concerning the viscosity of the medium surrounding the sensor, the oscillating amplitude of the oscillating element 12 must be measured. This can be easily determined by measuring the voltage U induced as a result of the magnetic field B and the oscillating movement of the oscillating element 12 at two opposite contact electrodes 14 with different oscillating frequencies, i.e. by recording a frequency response of the oscillation in the frequency range of interest (for example 500 Hz to 10 kHz). The voltage U induced in the oscillating element as a result of the oscillation in the magnetic field is used as a measure of the change (1st derivative with respect to time) of the oscillating amplitude. The damping factor D (=1/Q) of interest can be calculated from the frequency-dependent amplitude and phase response of the induced voltage U, and from it the viscosity η of the liquid surrounding the sensor can be concluded. The phase of the induced voltage U is measured in relation to the phase position of the input signal $U_{Ex}$ generated by the function generator. As an alternative to the frequency response of the induced voltage U, the frequency response of the (complex) impedance may also be measured, that is to say the frequency response $U/i_{Ex}$ of the ratio between the induced voltage U and the excitation current $i_{EX}$.

The induced voltage U may be badly affected by noise. Since, however, the frequency is known (it is the same as the frequency of the oscillation-exciting current $i_{EX}$), a lock-in amplifier can be used for measuring the amplitude and the phase of the induced voltage, making it is possible to measure signals even with very unfavorable signal-to-noise ratios (SNR).

Figure 1:
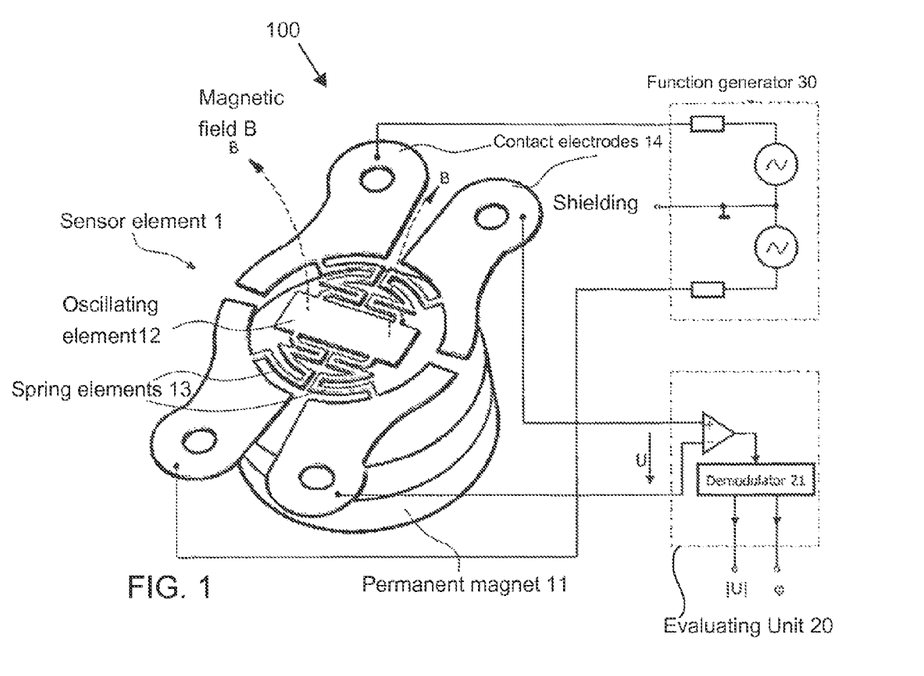
FIG. 1 shows a perspective representation of a first exemplary embodiment of the viscosity sensor according to the invention with the associated electronic circuitry.
Figure 2A:
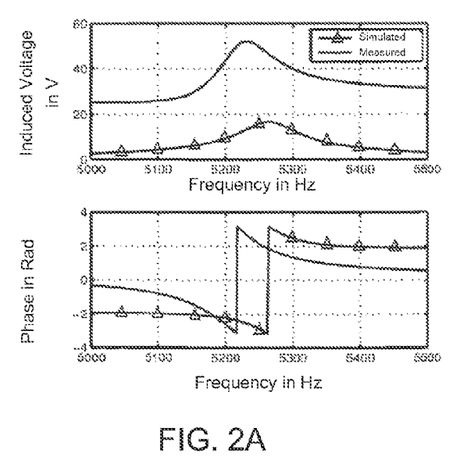

Measurement results given by way of example and obtained with the sensor arrangement 100 from FIG. 1 are represented for example in FIG. 2. FIG. 2 a shows the frequency response (amplitude and phase response) of the induced voltage U when water was used as the viscous fluid. The viscosity of water at 20° C. is around 1 mPa·s. The measured resonant frequency of the sensor element 1 is around 5230 Hz. The damping of the oscillating circuit is characterized by the damping factor D, the damping factor D being the inverse of the quality factor Q of the resonance.

Figure 2B:
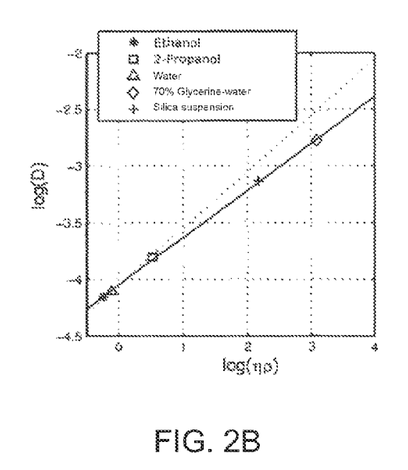

FIG. 2 b shows in log-log representation the relationship between the damping factor D and the viscosity-density product ηρ for different liquids, the symbol η denoting the dynamic viscosity in Pa·s and the symbol ρ denoting the density of the viscous fluid in kg/m³. In the (log-log) representation, an (approximately) linear relationship can be seen between the logarithm of the damping factor $\log_{10}(D) = -\log_{10}(Q)$ and the logarithm of the viscosity-density product $\log_{10}(\eta\rho)$.

The sensor element 1 from FIG. 1 is excited by a current $i_{EX}$ which flows by way of the two contact electrodes 14 on the left and the spring elements 13 on the left connected thereto. The induced voltage is picked off at the two contact electrodes 13 on the right, which are electrically connected to the oscillating element 12 by way of the spring elements 13 on the right that are connected thereto. With a magnetic field B, which passes approximately perpendicularly through the oscillating element 12, an in-plane oscillation (oscillation in the plane of the plate) is mainly obtained as a result. It has been found that only with in-plane oscillations—as opposed to oscillations normal to the plane of the plate (out-of-plane oscillations)—can a clearly defined relationship between viscosity and damping be observed (cf. FIG. 1 b).

Figure 3:
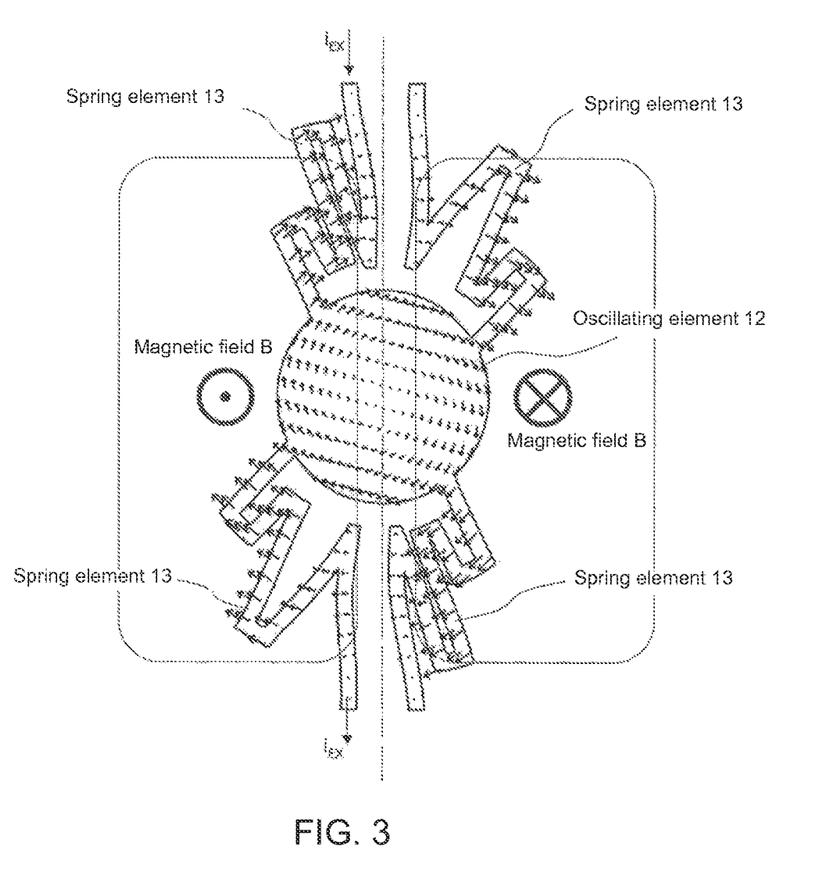
FIG. 3 shows a second exemplary embodiment of the viscosity sensor according to the invention (plan view), in which the oscillating body is disposed in an inhomogeneous magnetic field in such a way that a rotational oscillation is obtained (the deformation of the oscillating element is shown exaggerated)

A further exemplary embodiment of the sensor element 1, in which the oscillating element 12 performs a rotary in-plane oscillation, is represented in FIG. 3. In the diagram presented, to simplify matters only the oscillating element 12 and the spring elements 13 are shown in a plan view. By contrast with the example from FIG. 1, the oscillating element 12 is not a rectangular plate but a circular plate, and the magnetic field B passes through the plate inhomogeneously. In the present case, the magnetic field B passes through the plane of the plate of the oscillating element 12 normal to the plane of the plate. The direction of the magnetic field B in the left half of the oscillating element 12 is exactly opposed to the direction in the right half. The sensor element 1 is to this extent "antisymmetric", which is represented by the dash-dotted line of symmetry.

Figure 5:
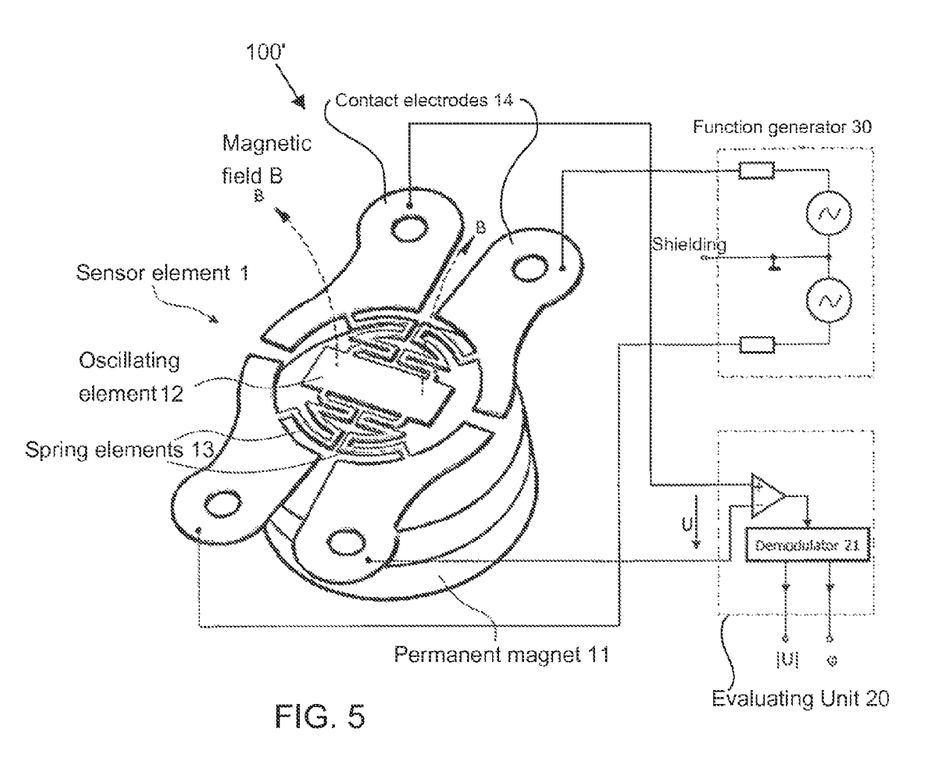
FIG. 5 shows a perspective representation of another exemplary embodiment of the viscosity sensor.

FIG. 5 shows an embodiment of the sensor arrangement 100' in which the oscillating element 12 is mounted with the aid of four spring elements 13, two diagonally opposite spring elements 13 being used for feeding in the excitation current $i_{EX}$ and the two remaining spring elements being used for picking off the induced voltage U. In the case of this exemplary embodiment, the activation of the sensor element 1 and the evaluation of the induced voltage U take place by analogy with the example from FIG. 1. The arrows in FIG. 2 show the (simulated) (Lorentz) force effect on the oscillating element 12 on account of an excitation current $i_{EX}$. It can be clearly seen that such a force effect excites an in-plane rotational oscillation of the plate-shaped oscillating element 12. This in-plane rotational oscillation has minor out-of-plane movement components, which however always occur in practice. As already mentioned, an oscillation that is as purely in-plane as possible is desirable with regard to a simple relationship between the damping factor D and the viscosity-density product rip.

An out-of-plane oscillation may be desirable if it is intended at the same time (or alternatively) to measure the density of the fluid. This case will also be discussed more precisely at the end.

Figure 4:
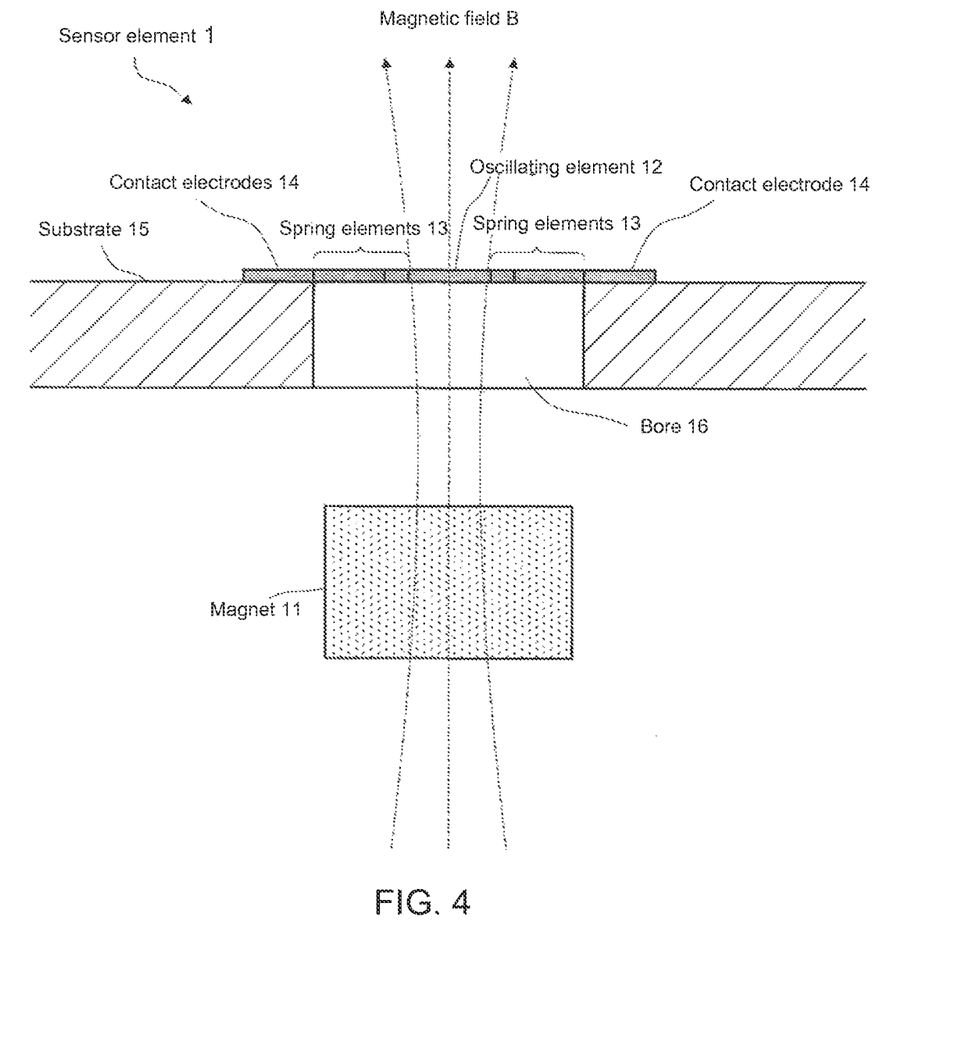
FIG. 4 shows a schematic sectional representation of the sensor arrangement from FIG. 3.

For better understanding, a sectional representation of the sensor element 1 from FIG. 3 is depicted in FIG. 4. The section is taken through the line of symmetry from FIG. 3. Disposed on a carrier substrate 15 (printed circuit board, ceramic substrate, etc.) is a thin metallization layer (components 12, 13 and 14) of the order of magnitude of 100 μm in thickness. In the production of the sensor element 1, a metal foil, for example, may be applied to the substrate 15 and subsequently structured with the aid of wet etching or laser cutting in such a way that the structure shown in FIG. 1 or 3, comprising the oscillating element 12, spring elements 13 and contact electrodes 14, is created. In the substrate there is a through-hole 16 with a diameter of around 5 mm to 10 mm, which is partially covered at one end by the oscillating element 12 and the spring elements 13. The plate-shaped oscillating element 12 is therefore only connected to the contact electrodes 14 disposed on the substrate 15 by way of the spring elements 13, so that the viscous liquid can contact the oscillating element 12 from both sides and make it oscillate freely in the liquid.

The magnet 11 may be secured to the substrate 15 by way of spacers (not represented), so that the liquid is not hindered from entering the bore 16. In alternative exemplary embodiments of the invention, the magnet 11 may also be disposed outside the liquid. With an annular magnet, which is disposed concentrically in relation to the bore 16 in the vicinity of the substrate 15, a good geometry of the magnetic field lines can be achieved, whereby in turn undesired out-of-plane components of the oscillating movement of the oscillating element 12 are reduced.

The exemplary embodiments of the invention that are represented in the figures all have 4 contact electrodes 14, which are each connected to the oscillating element 12 by way of a spring element 13. The excitation current $i_{EX}$ is fed into the oscillating element 12 by way of two respective contact electrodes and spring elements and the induced voltage U is picked off by way of the two other contact electrodes and spring elements. However, it is also possible to use the same contact elements for feeding in the excitation current $i_{EX}$ and for measuring the induced voltage U, so that in principle two spring elements 13 would suffice. Also possible are sensor arrangements with three spring elements, in which only one contact electrode is used for the dual function of carrying the excitation current and picking off the voltage. In the case of such arrays, the induced alternating voltage U is however superposed by a relatively great direct component, which makes measuring the voltage more difficult. In this case, the use of a measuring bridge may be necessary for measuring the voltage. In practical tests, better results were achieved with the variant with four spring elements.

In the case of the exemplary embodiments discussed above, the magnetic field B passes through the oscillating element approximately at a right angle, which is conducive to the excitation of in-plane oscillating modes (translatory or rotary) and avoids out-of-plane oscillating modes. For a viscosity measurement it is favorable to excite as far as possible only in-plane oscillating modes. In some applications, however, it may also be advisable to align the magnetic field in such a way that it also has components in the plane of the plate of the oscillating element 12, so that out-of-plane oscillating modes are excited.

In-plane oscillating modes and out-of-plane oscillating modes have different resonant frequencies, so that, if both oscillating modes are excited, in the measured frequency response there can be detected two resonances, which can be evaluated independently of each other. As explained above—the resonance of the in-plane oscillating mode is used for calculating the viscosity η or the viscosity-density product ηρ. The resonant frequency of the out-of-plane oscillating mode can be used to calculate the density ρ. The relationship between the resonant frequency of a spring-mass-damper system and the oscillating mass (or the density of the liquid) is known per se. The spring-mass-damper model may also be used for calculating the density.

The in-plane and out-of-plane oscillating modes are superposed linearly and can therefore be considered separately from each other. With a sensor arrangement 100 according to one of the examples from FIGS. 1, 3 and 4, it is also possible, depending on the orientation of the magnetic field, to measure viscosity, density or both.

FIG. 1 shows an evaluating unit 20 connected to the contact electrodes 14 and configured to pick off, by way of the contact electrodes 14 and the spring elements 13, a voltage induced in the oscillating plate and to provide a measured value for a voltage amplitude of the voltage and/or for a phase of the voltage in relation to the excitation current. The evaluating unit 20 can be configured to vary the frequency of the excitation current over a prescribed frequency range, and to thus determine a frequency response of the induced voltage in the prescribed frequency range. The prescribed frequency range lies in a range from 500 Hz to 20 kHz. The evaluating unit 20 can be configured to determine a frequency response of a ratio between the induced voltage and the excitation current in a prescribed frequency range. The prescribed frequency range lies in a range from 500 Hz to 20 kHz. The evaluating unit 20 can be configured: to detect at least one resonance in a measured frequency response of the induced voltage; to determine for each detected resonance at least one characteristic value characterizing the resonance; and depending on the at least one characteristic value, to calculate one or more properties describing the physical behavior of the liquid. The evaluating unit 20 can be configured to detect a resonance in the measured frequency response, to determine a damping coefficient describing the damping of the resonance and, depending on the damping coefficient, to calculate a viscosity of the liquid. The evaluating unit 20 can be configured to detect a second resonance in the measured frequency response, to determine a corresponding resonant frequency and, depending on the resonant frequency, to calculate a density of the liquid. The evaluating unit 20 can be configured to detect a first and a second resonance in the measured frequency response, to determine a damping coefficient, describing the damping of the first resonance, and the resonant frequency of the second resonance, and, depending on the resonant frequency of the second resonance, to calculate the density of the liquid and, depending on the damping coefficient of the first resonance, to calculate the viscosity of the liquid.

Figure 6:
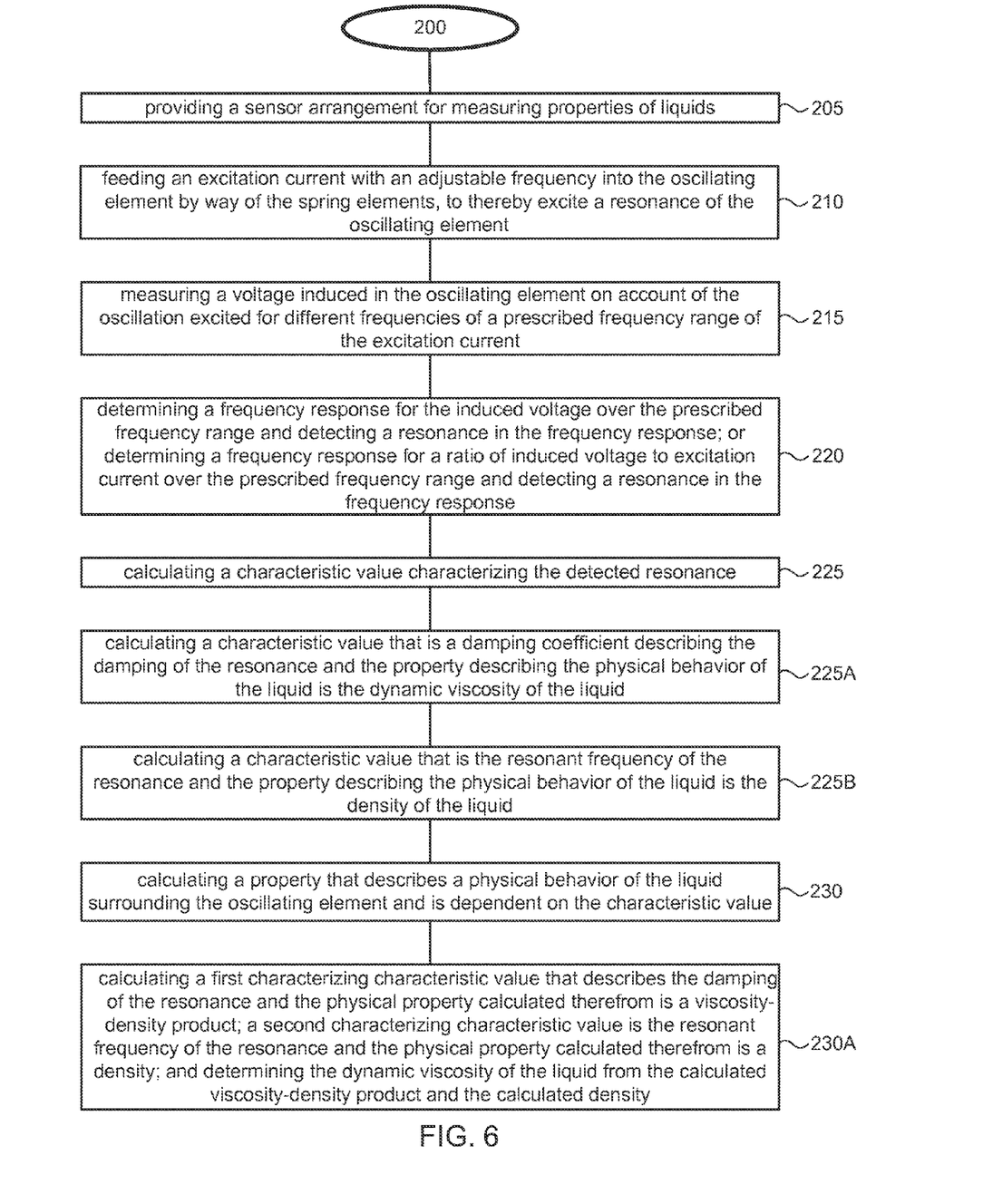
FIG. 6 is a block diagram showing the steps of a method.

FIG. 6 is a block diagram showing the steps of a method 200 of measuring properties, such as, the viscosity and/or a density of a liquid. Step 205 includes providing the sensor arrangement disclosed herein. Step 210 includes feeding an excitation current with an adjustable frequency into the oscillating element by way of the spring elements, to thereby excite a resonance of the oscillating element. Step 215 includes measuring a voltage induced in the oscillating element on account of the oscillation excited for different frequencies of a prescribed frequency range of the excitation current. Step 220 includes performing one of the following steps: determining a frequency response for the induced voltage over the prescribed frequency range and detecting a resonance in the frequency response; or determining a frequency response for a ratio of induced voltage to excitation current over the prescribed frequency range and detecting a resonance in the frequency response. Step 225 includes calculating a characteristic value characterizing the detected resonance. Step 225A includes calculating a characteristic value that is a damping coefficient describing the damping of the resonance and the property describing the physical behavior of the liquid is the dynamic viscosity of the liquid. Step 225B includes calculating a characteristic value that is the resonant frequency of the resonance and the property describing the physical behavior of the liquid is the density of the liquid. Step 230 includes calculating a property that describes a physical behavior of the liquid surrounding the oscillating element and is dependent on the characteristic value. Step 230A includes calculating a first characterizing characteristic value describes the damping of the resonance and the physical property calculated therefrom is a viscosity-density product; a second characterizing characteristic value is the resonant frequency of the resonance and the physical property calculated therefrom is a density; and determining the dynamic viscosity of the liquid from the calculated viscosity-density product and the calculated density.

The invention claimed is:

1. A sensor arrangement for measuring properties of liquids, the sensor arrangement comprising:
   a carrier substrate formed with an opening, said carrier substrate having a surface;
   a metal, plate-shaped oscillating element disposed on said surface of said carrier substrate, over said opening, and parallel to said surface, said plate-shaped oscillating element consisting completely of metal;
   at least two metal spring elements mounting said oscillating element on said carrier substrate;
   at least two electrically conductive contact electrodes disposed on said carrier substrate and electrically connected to said oscillating element by way of said metal spring elements;
   a magnet disposed in a vicinity of said carrier substrate and oriented such that magnetic field lines from said magnet pass through said plate-shaped oscillating element; and
   an evaluating unit coupled to the oscillating element via two of the at least two metal springs.

2. The sensor arrangement according to claim 1, wherein a property of a liquid to be measured is a viscosity of the liquid; and
   the magnetic field lines pass through said plate-shaped oscillating element in such a way that, when an excitation current is fed into said oscillating element by way of at least two of said contact electrodes, said plate-shaped oscillating element is excited to perform an in-plane oscillation.

3. The sensor arrangement according to claim 1, which further comprises an activating unit connected to said contact electrodes and configured to feed an excitation current with an adjustable frequency into said oscillating element by way of at least two of said contact electrodes and said spring elements.

4. The sensor arrangement according to claim 3, wherein the evaluating unit is connected to at least two of said contact electrodes and configured to pick off, by way of at least two of said contact electrodes and said spring elements, a voltage induced in said oscillating plate and to provide a measured value for a voltage amplitude of the voltage and/or for a phase of the voltage in relation to the excitation current.

5. The sensor arrangement according to claim 4, wherein said evaluating unit is configured to vary the frequency of the excitation current over a prescribed frequency range, and to thus determine a frequency response of the induced voltage in the prescribed frequency range.

6. The sensor arrangement according to claim 5, wherein the prescribed frequency range lies in a range from 500 Hz to 20 kHz.

7. The sensor arrangement according to claim 4, wherein said evaluating unit is configured to determine a frequency response of a ratio between the induced voltage and the excitation current in a prescribed frequency range.

8. The sensor arrangement according to claim 7, wherein the prescribed frequency range lies in a range from 500 Hz to 20 kHz.

9. The sensor arrangement according to claim 4, wherein said evaluating unit is configured:
to detect at least one resonance in a measured frequency response of the induced voltage;
to determine for each detected resonance at least one characteristic value characterizing the resonance; and
depending on the at least one characteristic value, to calculate one or more properties describing the physical behavior of the liquid.

10. The sensor arrangement according to claim 9, wherein the physical behavior of the liquid is a viscosity or a density thereof.

11. The sensor arrangement according to claim 1, wherein said magnet is disposed such that the magnetic field lines pass through said plate-shaped oscillating element approximately perpendicular to a plane of the plate in which said oscillating element lies.

12. The sensor arrangement according to claim 11, wherein said evaluating unit is configured to detect a resonance in the measured frequency response, to determine a damping coefficient describing the damping of the resonance and, depending on the damping coefficient, to calculate a viscosity of the liquid.

13. The sensor arrangement according to claim 1, wherein the magnetic field lines have components in a plane of said plate of said oscillating element, to thereby excite an out-of-plane oscillation of said oscillating element.

14. The sensor arrangement according to claim 13, wherein said evaluating unit is configured to detect a second resonance in the measured frequency response, to determine a corresponding resonant frequency and, depending on the resonant frequency, to calculate a density of the liquid.

15. The sensor arrangement according to claim 1, wherein the magnetic field lines have components in a plane of said plate and normal to the plane of said plate of said oscillating element, to thereby excite an out-of-plane oscillation and an in-plane oscillation of said oscillating element.

16. The sensor arrangement according to claim 15, wherein said evaluating unit is configured to detect a first and a second resonance in the measured frequency response, to determine a damping coefficient, describing the damping of the first resonance, and the resonant frequency of the second resonance, and, depending on the resonant frequency of the second resonance, to calculate the density of the liquid and, depending on the damping coefficient of the first resonance, to calculate the viscosity of the liquid.

17. The sensor arrangement according to claim 1, wherein said contact electrodes are four contact electrodes and said spring elements are four spring elements, by way of which said oscillating element is electrically connected to said contact electrodes and mechanically mounted thereon, and wherein said contact electrodes and said spring elements being disposed symmetrically about an axis of symmetry of said oscillating element.

18. The sensor arrangement according to claim 17, wherein the excitation current is conducted through said oscillating element by way respectively of two of said four spring elements, and a voltage induced in said oscillating element is picked off for voltage measurement by way of the other said two spring elements.

19. The sensor arrangement according to claim 18, wherein the excitation current is conducted through said oscillating element by way of two spring elements that are located on a same side of the axis of symmetry, so as to excite a translatory in-plane oscillation of said oscillating element.

20. The sensor arrangement according to claim 18, wherein the excitation current is conducted through said oscillating element by way of two said spring elements, wherein one of said two spring elements is located diagonally opposite the other of said two spring elements, so as to excite a rotary in-plane oscillation of said oscillating element.

21. The sensor arrangement according to claim 1, comprising exactly two said contact electrodes and exactly two said spring elements, by way of which said oscillating element is electrically connected to said contact electrodes and also mechanically mounted thereon, said contact electrodes and said spring elements being disposed symmetrically around an axis of symmetry of said oscillating element.

22. The sensor arrangement according to claim 21, wherein the excitation current is conducted through said oscillating element by way of said two spring elements and the voltage induced in said oscillating element is picked off for voltage measurement by way of said same two spring elements.

23. The sensor arrangement according to claim 1, which further comprises a non-conductive layer disposed on said plate-shaped oscillating element.

24. A method of measuring properties of a liquid, the method which comprises:
providing a sensor arrangement for measuring properties of liquids, the sensor arrangement comprising:
a carrier substrate formed with an opening, said carrier substrate having a surface,
a metal, plate-shaped oscillating element disposed on said surface of said carrier substrate, over said opening, and parallel to said surface, said plate-shaped oscillating element consisting completely of metal,
at least two metal spring elements mounting said oscillating element on said carrier substrate,
at least two electrically conductive contact electrodes disposed on said carrier substrate and electrically connected to said oscillating element by way of said metal spring elements,
a magnet disposed in a vicinity of said carrier substrate and oriented such that magnetic field lines from said magnet pass through said plate-shaped oscillating element, and
an evaluating unit coupled to the oscillating element via two of the at least two metal springs;
feeding an excitation current with an adjustable frequency into the oscillating element by way of the spring elements, to thereby excite a resonance of the oscillating element;
measuring a voltage induced in the oscillating element on account of the oscillation excited for different frequencies of a prescribed frequency range of the excitation current;
performing one of the following steps:
determining a frequency response for the induced voltage over the prescribed frequency range and detecting a resonance in the frequency response; or
determining a frequency response for a ratio of induced voltage to excitation current over the prescribed frequency range and detecting a resonance in the frequency response;

calculating a characteristic value characterizing the detected resonance; and calculating a property that describes a physical behavior of the liquid surrounding the oscillating element and is dependent on the characteristic value.

25. The method according to claim 24, which comprises measuring a viscosity and/or a density of the liquid.

26. The method according to claim 24, wherein the characterizing characteristic value is a damping coefficient describing the damping of the resonance and the property describing the physical behavior of the liquid is the dynamic viscosity of the liquid.

27. The method according to claim 24, wherein the characterizing characteristic value is the resonant frequency of the resonance and the property describing the physical behavior of the liquid is the density of the liquid.

28. The method according to claim 24, wherein:

a first characterizing characteristic value describes the damping of the resonance and the physical property calculated therefrom is a viscosity-density product;

a second characterizing characteristic value is the resonant frequency of the resonance and the physical property calculated therefrom is a density; and the dynamic viscosity of the liquid is determined from the calculated viscosity-density product and the calculated density.

29. The method according to claim 24, which further comprises disposing a non-conductive layer on said plate-shaped oscillating element.

\* \* \* \* \*